Figure 1:
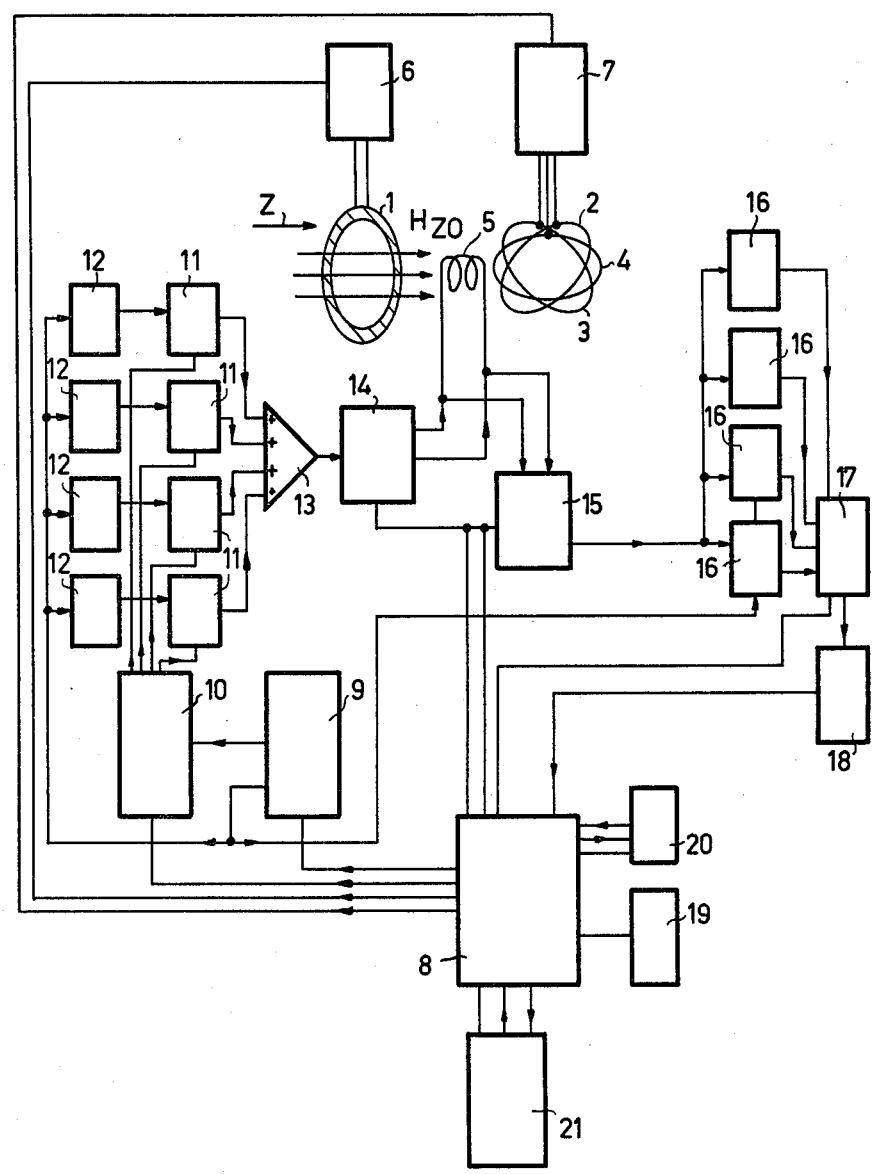

United States Patent [19]

Heinzerling et al.

[11] 4,276,529
[45] Jun. 30, 1981

[54] MAGNET COIL ARRANGEMENT FOR GENERATING A HOMOGENEOUS MAGNETIC FIELD FOR MAGNETIC RESONANCE ARRANGEMENTS

[75] Inventors: Jürgen Heinzerling, Hamburg; Rainer Rieckeheer, Quickborn, both of Fed. Rep. of Germany

[73] Assignee: U.S. Philips Corporation, New York, N.Y.

[21] Appl. No.: 93,969

[22] Filed: Nov. 14, 1979

[30] Foreign Application Priority Data

Nov. 14, 1978 [DE] Fed. Rep. of Germany ....... 2849355

[51] Int. Cl.³ ............................................. H01F 5/00
[52] U.S. Cl. ...................................... 335/300; 336/60
[58] Field of Search ............... 335/209, 216, 299, 300; 313/62; 336/60

[56] References Cited

U.S. PATENT DOCUMENTS 4,084,209  4/1978  Hilal et al. .......................... 335/216

*Primary Examiner*—George Harris
*Attorney, Agent, or Firm*—Thomas A. Briody; Robert T. Mayer; Jack E. Haken

[57] ABSTRACT

The invention relates to a magnet coil arrangement for generating a magnetic field which is homogeneous at least in its center, preferably for magnetic resonance spectroscopy. The arrangement consists of four flat ring coils whose coil planes extend perpendicularly to an axis of examination which extends through the coil centers. The coils are symmetrically arranged with respect to a point situated on this axis. By means of a magnetic coil arrangement of this kind, a magnetic field can be generated which extends in the direction of the axis of examination and rotationally-symmetrically with respect thereto and which, in comparison with the magnetic fields generated by means of known coil arrangements, has an improved homogeneity in the direction perpendicular to the axis of examination over a larger range which extends in the direction perpendicular to the axis of examination in the center of the magnetic coil arrangement.

2 Claims, 4 Drawing Figures

MAGNET COIL ARRANGEMENT FOR GENERATING A HOMOGENEOUS MAGNETIC FIELD FOR MAGNETIC RESONANCE ARRANGEMENTS

The invention relates to a magnet coil arrangement for generating a magnetic field which is homogeneous at least in its centre, preferably for magnetic resonance spectroscopy, consisting of four flat, pair-wise identical ring coils, the coil planes of the ring coils extending perpendicularly to an axis of examination which extends through the coil centres and the coils being symmetrically arranged with respect to a central point on the axis of examination axis, the ring coils which belong to different pairs having different mean winding diameters as well as rectangular winding cross-sections, the sides of which extend perpendicularly and parallel, respectively to the axis of examination, the coil pair having the larger mean winding diameter being situated in between the coils of the pair having the smaller mean winding diameter, current flowing in the same direction, through all ring coils.

A magnet coil arrangement of this kind is known, for example, from the article "Axially Symmetric Systems for Generating and Measuring Magnetic Fields", by M. W. Garrett, published in Appl. Phys., September 1951. Using this arrangement, and assuming vanishingly small winding cross-sections, a rotationally symmetrical magnetic field B can be generated which extends in the direction of an axis of examination and which has a homogeneity perpendicularly to the examination axis of $\Delta B/B = 10^{-4}$ in a zone in the centre of the coil arrangement surrounding the axis of examination. Therein, $\Delta B$ denotes the local fluctuation of the magnetic field B perpendicularly to the axis of examination.

For generating stronger magnetic fields, however, comparatively large winding cross-sections must be used for the individual ring coils in view of the limited current loadability of the winding material to be used. From Review of Scientific Instruments, Vol. 33, 1962, page 933, it is known that notably the shape and the size of the winding cross-sections have an effect on the homogeneity of the magnetic field in the magnet coil arrangement.

The invention has for its object to provide a magnet coil arrangement by means of which strong magnetic fields having an improved homogeneity perpendicularly to the axis of examination in comparison with the known arrangements can be generated in a zone extending as far as possible in the direction perpendicular to the axis of examination.

This object is realized in accordance with the invention in that the mean winding diameter of the smaller ring coils amounts to approximately 0.635 times the mean winding diameter of the larger ring coils and the axial winding width of all ring coils amounts to approximately 0.084 times this value, the radial winding height of the larger ring coils amounting to approximately 0.162 times the mean winding diameter of the larger ring coils, the radial winding height of the smaller ring coils amounting to approximately 0.100 times this diameter, the distance between the central plane of the larger ring coils and the central point amounting to approximately 0.144 times this diameter, and the distance between the central plane of the smaller ring coils and the central point amounting to approximately 0.376 times this diameter, the number of ampere-turns of the larger ring coils being at least approximately 1.65 times the number of ampere-turns of the smaller ring coils.

Each individual ring coil whose coil plane extends perpendicularly to an axis of examination which extends through the centres of the ring coils has a rectangular winding cross-section, the sides of which extend parallel or perpendicularly to the axis of examination. The mean winding diameter of a ring coil is then the distance between the centres of winding cross-sections which are situated opposite each other in a plane which contains the axis of examination.

By means of a magnet coil arrangement of this kind it is achieved, when the individual ring coils are accurately proportioned and positioned, that the magnetic field extending in the direction of the axis of examination and rotationally-symmetrically with respect thereto, has a homogeneity perpendicular to the axis of examination of $10^{-5}$ in the centre of the magnetic coil arrangement up to a distance of approximately 13.9% of the larger mean winding diameter from the axis of examination, and a homogeneity perpendicular to the axis of examination of $10^{-4}$ up to a distance of approximately 17.3% of the larger mean winding diameter from the axis of examination.

It is important that for predetermined mean winding diameters of the larger ring coils, the winding diameter of the smaller ring coils may deviate from the determined value by only less than 0.3% for a predetermined position on the axis or examination, whilst the winding heights and winding width may fluctuate up to plus or minus 3% around their determined values, without the homogeneity properties of the magnet coil arrangement being affected thereby. However, the required ratio of the numbers of ampere-turns of the larger and the smaller ring coils should remain at least approximately constant. The distances between the central planes of the ring coils and the centre point are then defined by the mean winding diameter of the larger ring coils and must be adhered to with an accuracy of better than 0.1%.

The examination zone, that is to say the radial extent of the homogeneous magnetic field in the centre of the magnet coil arrangement, can be increased or decreased by a corresponding linear increase or decrease of the dimensions of the magnet coil arrangement (or the ring coil dimensions), so that in view of saving of costs and weight a magnet coil arrangement in accordance with the dimensions of the body each time to be examined thereby can be formed.

The intensity of the magnetic field in the examination zone is limited by the highest permissible current density of the conductor material of the ring coil windings, which in its turn is dependent of the cooling of the ring coils used.

Magnet coil arrangements of this kind are preferably used for magnetic resonance spectroscopy for determining the interior structure of a body. As has already been described in German Offenlegungsschrift No. 27 55 956, the nuclear induction signals originating from different parts of the body are separated from each other by different resonant frequencies of the nuclear spins in the body. The resonant frequency is determined by the intensity of a magnetic field which penetrates the body and which is composed of a substantially homogeneous magnetic field which extends in the direction of the axis of examination, rotationally-symmetrically with respect thereto, perpendicularly to the axis of examination, and of further, adjustable magnetic gradient fields having constant magnetic field gradients. Preferably, for a three-dimensionsal examination of the body, two magnetic field gradients which extends perpendicularly with respect to each other extend each time perpendicularly to the direction of the homogeneous magnetic field, whilst a third magnetic field gradient extends in the direction of the homogeneous magnetic field. Using the magnetic field (homogeneous magnetic field and magnetic gradient fields), defined zones of the body to be examined can be excited, so that the nuclear induction signals obtained can be unambiguously associated with the body zones emitting these signals.

The better the homogeneous magnetic field is, the smaller the magnetic gradient fields to be superposed on this field may be, without the unambiguity between nuclear induction signal and associated body zone being lost. Because the gradient fields are periodically superposed on the homogeneous magnetic field, an advantage is obtained in that no excessive induction peaks occur when the gradient fields are switched.

As a result of the small extent of the gradient fields, a further advantage is obtained in that the decay time of the nuclear induction signal which is periodically excited by high frequency pulses is increased. This means that the exponentially decreasing amplitude of the nuclear induction signal reaches a value corresponding to the amplitude of the noise signals only after a prolonged period of time. Thus, in comparison with signals having short decay times, a nuclear induction signal has a larger data content, so that a body zone to be examined need be excited less often. The total scanning time of a body is thus substantially reduced.

In a preferred embodiment in accordance with the invention, the ring coils are made of current conductors having a rectangular, hollow profile.

The ring coils can thus be simply cooled by conducting a cooling medium, for example, water, through the interior of the conductors. The current density in the ring coils can then be further increased, so that stronger magnetic fields can be generated inside the coil arrangement.

The drawing shows an embodiment in accordance with the invention.

Figure 2:
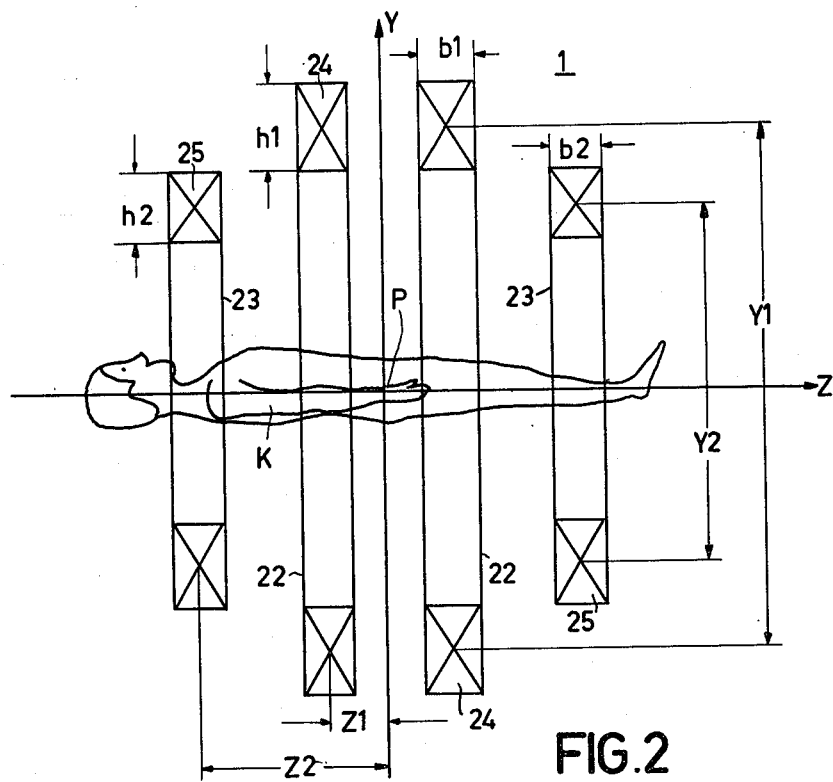
Figure 3A:
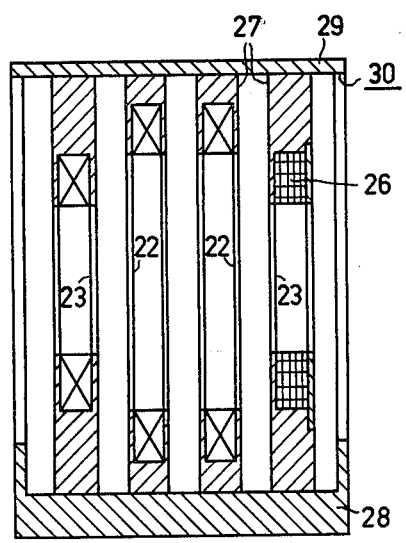

FIG. 1 is a block diagram of a device for determining the interior body structure by means of magnetic resonance spectroscopy, FIG. 2 diagrammatically shows a magnet coil arrangement in accordance with the invention, and FIGS. 3a, b, are a side elevation and a front view, respectively, of a mechanical mount for the magnet coil arrangement.

FIG. 1 shows a block diagram of an apparatus for determining the nuclear spin density distribution of a body. Therein, a magnet coil arrangement 1 (see FIG. 2) which is only diagrammatically shown generates a homogeneous magnetic field Hzo which extends in the direction of a coordinate axis Z of a three-dimensional, orthogonal system of coordinates SYZ and which penetrates a body K (see FIG. 2) arranged in the interior of the magnet coil arrangement 1. The body K, being positioned, for example, on a patient table, is slidable with respect to the magnet coil arrangment 1 in the direction of the coordinate axis Z which represents the axis of examination. Three gradient coils 2, 3 and 4 generate sufficiently constant magnetic field gradients $\partial Hz/\partial x$, $\partial Hz/\partial y$ and $\partial Hz/\partial z$, all field gradients being separately adjustable. The nuclear spin is excited and the nuclear induction (nuclear resonance) signals are measured by means of a high frequency coil 5. The gradient coils 2, 3 and 4 as well as the high frequency coil 5 enclose the body K to be examined (FIG. 2) at the area of the magnet coil arrangement 1. The magnet coil arrangement 1 and the gradient coils 2–4 are powered by mains apparatus 6 and 7 which are controlled by an electronic unit 8 (arithmetic and control unit). The electronic unit 8 controls the entire measuring process and subsequently serves for reconstructing images representing the interior structure of the body K.

The high frequency signal required for excitation of the nuclear spins is derived from a frequency synthesizer 9 which also controls a pulse generator 10 which is required for generating a modulation signal. The pulse generator 10 determines, via the modulation signal and by means of the modulators 11, the duration and the frequency bandwidth of the high frequency signal which excites the nuclear spins and which may consist of a plurality of phase-shifted components which are generated by the phase shifter 12. The phase-shifted components of the high frequency signal are added in the adder 13. A high frequency power amplifier 14 supplies the high frequency coil 5 with the high frequency energy required for excitation of the nuclear spins, the pulse power being between 0.05 and 1 1 kilowatt, depending on the measuring process and the size of the body.

After successful excitation of the nuclear spins, the high frequency coil 5 receives the nuclear induction signal. This signal passes through a further high frequency amplifier 15, after which it is demodulated in the demodulators 16. An analog-to-digital converter 17 converts the demodulated nuclear induction signal into digital form. A subsequent signal averaging device 18 can improve the signal-to-noise ratio of different nuclear induction signals if the measuring cycle is repeated. The device 18 can also be used as a digital buffer memory.

Using the electronic unit 8, the desired body images can be formed from the nuclear induction signals in known manner, it being possible to display said images on a monitor 19 or to store these images in digital form on a disc memory 20. The complete system is controlled via a data input/output device 21.

FIG. 2 is a detailed view of the magnet coil arrangement 1 in accordance with the invention. The arrangement comprises two inner ring coils 22 and two outer ring coils 23, the coil planes of which extend perpendicularly to the axis of examination Z which extends through the coil centres. The ring coils 22 and 23 are symmetrically arranged with respect to a central point P which is fixed on the axis of examination and which represents, for example, the origin of the orthogonal three-dimensional system of coordinates XYZ.

The inner ring coils 22 have rectangular winding cross-sections 24, the sides of which extend parallel to the axis of examination Z (i.e. in the axial direction) or perpendicularly thereto, their axial winding width b1 being 112 mm and their radial winding height h1 being 216 mm. The mean winding diameter Y1 of the larger ring coils 22 amounts to 1332 mm, whilst the axial distance Z1 between their central planes and the central point P is 192 mm. The central plane is the plane in which the points of intersection of the diagonals of all winding cross-sections of a ring coil are situated.

The outer ring coils 23 also have rectangular winding cross-sections 25, the axial winding width b2 of which amounts to 112 mm whilst their radial winding height h2 amounts to 128 mm. The mean winding diameter Y2 of the ring coils is chosen to be 846 mm, whilst the axial distance Z2 between their central planes and the central point P is fixed at 501 mm.

Using the magnet coil arrangement 1 shown in FIG. 2, a magnetic field Bz can be generated which extends in the direction of the axis of examination Z, rotationally-symmetrically thereto, the magnetic field strength of said field amounting to, for example 0.1 tesla, said magnetic field surrounding the central point P with, up to a perpendicular distance of approximately 13.9% (185 mm) of the larger mean winding diameter Y1 from the axis of examination Z, a homogeneity perpendicular to the axis of examination of $\Delta Bz/Bz = 10^{-5}$, and with a homogeneity of $\Delta Bz/Bz = 10^{-4}$ perpendicular to the axis of examination up to a perpendicular distance of approximately 17.3% (230 mm) of the larger mean winding diameter Y1 from the axis of examination. The number of ampere-turns of the inner larger ring coils 22 is then approximately equal to 1.65 times the number of ampere-turns of the smaller outer ring coils 23.

The magnetic field strength which can be achieved by means of the magnet coil arrangement 1 is limited by the highest permissible current density of the conductor material of the ring coils 22, 23 which in its turn depends on the cooling of the coil windings. In order to enable comparatively strong magnetic fields to be generated with winding cross-sections which are not excessively large, hollow profile conductors 26 (see FIG. 3a) which may be made, for example, of copper or aluminium and which have, for example, a rectangular or a square cross-section, are used as the conductor material for the ring coils 22, 23. For cooling the ring coils 22, 23, a cooling medium, for example, water, is conducted through the hollow profile conductors 26. Obviously, the ring coils 22, 23 can also be cooled externally, for example, by means of cooling tubes wherethrough a cooling medium is conducted and which contact the ring coils 22, 23. The hollow profile conductors 26 for the larger and the smaller ring coils 22, 23, respectively, for example, have the same cross-sectional dimensions, so that the ring coils 22, 23 comprise different numbers of turns. Obviously, hollow profile conductors having different cross-sectional dimensions can also be used for the ring coils 22, 23. The required number of ampere-turns can then be adjusted by variation of the currents in the turns each time associated with a ring coil.

Figure 3B:
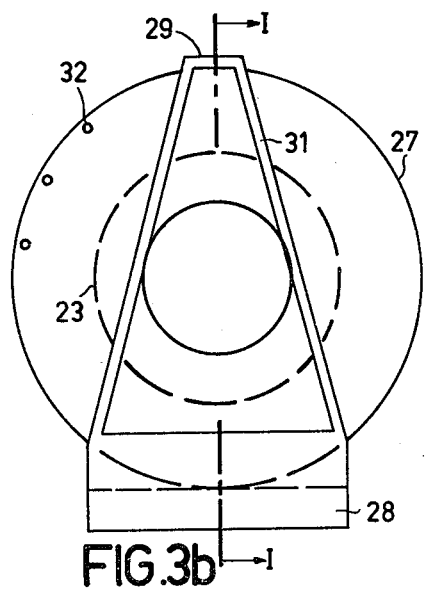

FIGS. 3a and b are a side elevation and a front view, respectively, of a mechanical mount for the magnet coil arrangement 1. The side elevation shown in FIG. 3a is a sectional view, taken along the line I—I, of the magnet coil arrangement 1 shown in FIG. 3b. The ring coils 22, 23 shown in the FIG. 3a are concentrically arranged in disc-shaped coil supports 27 in which they can be inserted, for example, laterally. The coil supports 27, being made of a magnetically non-conductive material, serve for stabilizing the shape of the ring coils 22, 23 and for the positioning thereof and are mounted in a mount 30 which consists of lower and upper supporting frames 28, 29 and which comprises lateral supporting elements 31 for the upper supporting frame 29. The coil supports 27 all have the same outer diameter and are rigidly connected to the lower and upper supporting frames 28, 29 after correct positioning. They furthermore comprise a concentric aperture, the diameter of which corresponds to the inner diameter of the relevant ring coils 22, 23, so that a body K (FIG. 2) to be examined can be slid into the interior of the magnet coil arrangement 1 while resting on a patient table. The coil supports 27 can furthermore be rigidly interconnected, as shown in FIG. 3b, by means of rods 32 which extend in the direction of the axis of examination Z while passing through the outer edge of the coil supports 27 and which maintain the supports at a distance from each other.

The embodiments of the invention in which an exclusive property of privilege is claimed are defined as follows:

1. A magnet coil arrangement for generating a magnetic field which is homogeneous at least in its centre, preferably for magnetic resonance spectroscopy, consisting of four flat, pair-wise identical ring coils, coil planes of the ring coils extending perpendicularly to an axis of examination which extends through the coil centres and the coils being symmetrically arranged with respect to a central point on the axis of examination, the ring coils which belong to different pairs having different mean winding diameters as well as rectangular winding cross-sections, the sides of which extend perpendicularly and parallel, respectively, to the axis of examination, the coil pair having the large mean winding diameter being situated between the coils of the pair having the smaller mean winding diameter, current flowing in the same direction through all ring coils, characterized in that the mean winding diameter of the smaller ring coils (23) amounts to approximately 0.635 times the mean winding diameter (Y1) of the larger ring coils (22) and the axial winding width (b) of all ring coils amounts to approximately 0.084 times this diameter, the radial winding height (41) of the larger ring coils amounting to approximately 0.162 times the mean winding diameter of the larger ring coils, the radial winding height (42) of the smaller ring coils (23) amounting to approximately 0.100 times this diameter, the distance (Z1) between the central plane of the larger ring coils and the central point (P) amounting to approximately 0.144 times this diameter, and the distance (Z2) between the central plane of the smaller ring coils and the central point amounting to approximately 0.376 times this diameter, the number of ampere-turns of the larger ring coils being at least approximately 1.65 times the number of ampere-turns of the smaller ring coils.

2. A magnet coil arrangement as claimed in claim 1, characterized in that the ring coils (22, 23) are wound from current conductors (26) having a rectangular, hollow profile.

* * * * *

UNITED STATES PATENT AND TRADEMARK OFFICE
CERTIFICATE OF CORRECTION

PATENT NO. : 4,276,529
DATED : June 30, 1981
INVENTOR(S) : JÜRGEN HEINZERLING et al It is certified that error appears in the above-identified patent and that said Letters Patent are hereby corrected as shown below:

Col 6, Line 32, Change "large" to read -- larger --

Signed and Sealed this

Seventeenth Day of August 1982

[SEAL]

Attest:

Attesting Officer

GERALD J. MOSSINGHOFF
Commissioner of Patents and Trademarks